United States Patent
Levin et al.

(10) Patent No.: US 8,006,365 B2
(45) Date of Patent: Aug. 30, 2011

(54) DEVICE AND METHOD FOR APPLYING ROTARY TACKS

(75) Inventors: Shalom Levin, Atlit (IL); Nir Altman, Kibbutz Kfar Etzion (IL)

(73) Assignee: EasyLap Ltd., Kfar Truman (IL)

( * ) Notice: Subject to any disclaimer, the term of this patent is extended or adjusted under 35 U.S.C. 154(b) by 883 days.

(21) Appl. No.: 12/022,240

(22) Filed: Jan. 30, 2008

(65) Prior Publication Data

US 2009/0188965 A1    Jul. 30, 2009

(51) Int. Cl.
*B23P 11/00* (2006.01)
*A61B 17/04* (2006.01)

(52) U.S. Cl. .............. 29/432; 227/175.1; 227/176.1; 227/175.2; 606/144

(58) Field of Classification Search .............. 29/432, 29/798; 227/175.1, 175.2, 176.1, 180.1, 227/73, 84; 606/139, 144, 219
See application file for complete search history.

(56) References Cited

U.S. PATENT DOCUMENTS

| | | | |
|---|---|---|---|
| 5,258,000 A | | 11/1993 | Gianturco |
| 5,312,023 A | * | 5/1994 | Green et al. .............. 227/175.1 |
| 5,810,882 A | * | 9/1998 | Bolduc et al. .............. 606/213 |
| 7,407,074 B2 | * | 8/2008 | Ortiz et al. .............. 227/175.1 |
| 7,481,348 B2 | * | 1/2009 | Marczyk .............. 227/176.1 |
| 7,703,653 B2 | * | 4/2010 | Shah et al. .............. 227/175.2 |
| 7,815,090 B2 | * | 10/2010 | Marczyk .............. 227/176.1 |
| 7,862,579 B2 | * | 1/2011 | Ortiz et al. .............. 606/205 |
| 7,879,070 B2 | * | 2/2011 | Ortiz et al. .............. 606/205 |
| 7,886,952 B2 | * | 2/2011 | Scirica et al. .............. 227/175.2 |
| 2006/0047306 A1 | | 3/2006 | Ortiz et al. |
| 2006/0047307 A1 | * | 3/2006 | Ortiz et al. .............. 606/219 |
| 2006/0047308 A1 | * | 3/2006 | Ortiz et al. .............. 606/219 |
| 2006/0129154 A1 | | 6/2006 | Shipp |
| 2008/0048002 A1 | * | 2/2008 | Smith et al. .............. 227/175.1 |
| 2008/0083807 A1 | * | 4/2008 | Beardsley et al. .............. 227/175.1 |
| 2008/0083809 A1 | * | 4/2008 | Scirica .............. 227/175.1 |
| 2008/0245842 A1 | * | 10/2008 | Marczyk .............. 227/179.1 |
| 2009/0065549 A1 | * | 3/2009 | Viola .............. 227/175.1 |
| 2009/0114699 A1 | * | 5/2009 | Viola .............. 227/175.1 |
| 2010/0001038 A1 | * | 1/2010 | Levin et al. .............. 227/179.1 |
| 2010/0163597 A1 | * | 7/2010 | Shah et al. .............. 227/175.1 |
| 2010/0200638 A1 | * | 8/2010 | Racenet et al. .............. 227/175.1 |
| 2010/0234687 A1 | * | 9/2010 | Azarbarzin et al. .............. 600/201 |
| 2010/0270354 A1 | * | 10/2010 | Rimer et al. .............. 227/175.1 |
| 2011/0062211 A1 | * | 3/2011 | Ross et al. .............. 227/175.1 |
| 2011/0062212 A1 | * | 3/2011 | Shelton et al. .............. 227/175.1 |

* cited by examiner

*Primary Examiner* — Essama Omgba
(74) *Attorney, Agent, or Firm* — Dekel Patent Ltd.; David Klein

(57) ABSTRACT

A tacker for applying a rotary tack, including a drive shaft coupled to a trigger, wherein operating the trigger causes rotation of the drive shaft, an articulated applicator arm pivotally connected to the drive shaft at a pivot, the articulated applicator arm including a rotatable output shaft connected to a magazine that holds a rotary tack, and a clutch mechanism which, at initial movement of the trigger, has a first orientation that causes the articulated applicator arm to pivot about the pivot until reaching a stop, and has a second orientation wherein upon continued movement of the trigger, the clutch mechanism permits the drive shaft to rotate the output shaft and cause application of the rotary tack from the magazine.

11 Claims, 15 Drawing Sheets

DEVICE AND METHOD FOR APPLYING ROTARY TACKS

FIELD OF THE INVENTION

The present invention relates generally to devices and methods for applying surgical fasteners, such as rotary tacks, to tissues, such as for hernia repairs and the like, and particularly to such devices and methods for use in laparoscopic and endoscopic procedures.

BACKGROUND OF THE INVENTION

A number of surgical procedures require instruments that are capable of applying a surgical fastener to tissue in order to form tissue connections or to secure objects to tissue. For example, during hernia repair it is often desirable to fasten a surgical mesh to the underlying body tissue. In laparoscopic procedures, such as for hernia repair, surgery is performed in the abdomen through a small incision, while in endoscopic procedures surgery is performed through narrow endoscopic tubes inserted through small incisions in the body. Laparoscopic and endoscopic procedures generally require long and narrow instruments capable of reaching deep within the body and configured to form a seal with the incision or tube through which they are inserted.

Currently, endoscopic techniques for hernia repair utilize fasteners, such as surgical staples or clips, to secure the mesh to the tissue thereby providing reinforcement of the repair and providing structure for the encouragement of tissue ingrowth. Another type of fastener suited for use in affixing mesh to tissue, during procedures such as hernia repair, is a coil fastener having a helically coiled body portion terminating in a tissue penetrating tip, in which the helical fastener is screwed into the mesh and body tissue. An example of this type of fastener is disclosed in U.S. Pat. No. 5,258,000 to Gianturco, assigned to Cook, Inc.

US Patent Application 20060129154 to John Shipp describes a trigger-operated mechanical tacker. Shipp uses another type of tack or screw-thread anchor that is screwed into the tissue. Shipp describes an anchor deliver device that has a handle, an actuator engaged with a rotator, an anchor retainer, an anchor advancer, a force reactor, and an anchor ejector for ejecting the anchors from the device. However, Shipp does not have a joint in the device, that is, the device has a long shaft with no bending or pivoting in the shaft. This is a disadvantage when trying to reach areas with difficult access thereto.

US Patent Application 20060047306 to Ortiz et al., assigned to Ethicon, describes a device for screwing in tacks to tissues and which has a joint in its elongate shaft. The device is not mechanical but electrically operated and uses an electroactive polymer actuator (EAP), which acts like an artificial muscle to pull or push things. In the Ethicon device, the EAP is coupled to a fastener advancing assembly such that energy delivery to the EAP causes movement of the fastener advancing assembly to advance a plurality of clips through the elongate shaft. The EAP is coupled to an articulation joint in the shaft and is adapted to move an end effector about the articulation joint relative to the elongate shaft when energy is delivered to the EAP.

SUMMARY OF THE INVENTION

The present invention seeks to provide devices and methods for applying surgical fasteners, such as rotary tacks, to tissues, such as for hernia repairs and the like, as is described more in detail hereinbelow. The device, herein referred to as a tacker, has a drive shaft with articulates with an applicator arm. Rotation of the drive shaft causes rotation of the articulated applicator arm and causes rotation of rotary tacks disposed in a magazine at the distal end of the articulated applicator arm, thereby screwing the tacks into tissue. The articulated applicator arm of the tacker pivots with respect to the drive shaft, thereby permitting the surgeon access to hard-to-reach places. The tacker of the invention pivots the articulated applicator arm and applies the rotary tacks all in one single, smooth squeeze of the trigger. Thus the tacker is very user-friendly for surgeons and can easily be used and manipulated with one hand, thereby freeing the other hand for other tasks. The tacker is dimensioned (e.g., 5 mm overall diameter for each of the drive shaft, articulated applicator arm and magazine housings) for easy entry into a trocar and the like.

There is thus provided in accordance with an embodiment of the present invention a tacker for applying a rotary tack, including a drive shaft coupled to a trigger, wherein operating the trigger causes rotation of the drive shaft, an articulated applicator arm pivotally connected to the drive shaft at a pivot, the articulated applicator arm including a rotatable output shaft connected to a magazine that holds a rotary tack, and a clutch mechanism which, at initial movement of the trigger, has a first orientation that causes the articulated applicator arm to pivot about the pivot until reaching a stop, and has a second orientation wherein upon continued movement of the trigger, the clutch mechanism permits the drive shaft to rotate the output shaft and cause application of the rotary tack from the magazine.

In accordance with an embodiment of the present invention a single full squeeze of the trigger causes the articulated applicator arm to pivot about the pivot and to rotate the output shaft and cause application of the rotary tack from the magazine.

Further in accordance with an embodiment of the present invention a drive gear is attached to a distal end of the drive shaft, and a spur gear is rotatingly mounted at the pivot and meshes with the drive gear and with a bevel gear attached to the output shaft of the articulated applicator arm, wherein upon initial rotation of the drive shaft, which starts rotating the spur gear, the clutch mechanism clutches the output shaft and does not permit rotation of the output shaft and the bevel gear such that rotation of the spur gear by the drive shaft causes the articulated applicator arm to pivot about the pivot until reaching the stop, and wherein continued rotation of the drive shaft further rotates the spur gear which imparts a turning force on the output shaft via the bevel gear that overcomes the clutch mechanism so that the clutch mechanism does not clutch the output shaft and the output shaft rotates and causes application of the rotary tack from the magazine. For example, the articulated applicator arm can pivot about the pivot until a proximal end of a housing of the articulated applicator arm abuts and stops against a distal end of a housing of the drive shaft.

In accordance with an embodiment of the present invention the magazine includes a housing in which a tacker shaft is journaled, the tacker shaft mating with a distal end of the output shaft, wherein the rotary tack is disposed along the tacker shaft, and wherein rotation of the output shaft causes rotation of the tacker shaft, thereby advancing the rotary tack off the tacker shaft. The drive shaft may be coupled to a distal end of a worm gear drive shaft journaled inside handle.

In accordance with an embodiment of the present invention the trigger is connected to a block, the block including one or more gear wheels which mesh with the worm gear drive shaft, wherein pulling the trigger proximally moves the block proximally, such that the one or more gear wheels turn and cause the worm gear drive shaft to rotate about its longitudinal axis, thus imparting rotation to the drive shaft. One or more return springs may be provided for urging the trigger distally.

In accordance with an embodiment of the present invention the block includes a ratchet mechanism including a pivoted ratchet toggle switch that has two positions, wherein one position allows the block to move only proximally and the other position allows the block to move only distally, and wherein when the trigger has been fully squeezed and the block has reached a proximal limit of its travel, the pivoted ratchet toggle switch pivots to the position that permits the trigger and the block to slide back distally.

Further in accordance with an embodiment of the present invention the trigger includes a safety mechanism that straightens the articulated applicator arm with respect to the drive shaft even if the trigger is released before reaching its proximal limit of travel.

There is also provided in accordance with an embodiment of the present invention a method for applying a rotary tack, including providing a drive shaft coupled to a trigger, wherein operating the trigger causes rotation of the drive shaft, an articulated applicator arm pivotally connected to the drive shaft at a pivot, the articulated applicator arm including a rotatable output shaft connected to a magazine that holds a rotary tack, and a clutch mechanism operatively connected to the trigger, and operating the trigger, wherein at initial movement of the trigger, the clutch mechanism has a first orientation that causes the articulated applicator arm to pivot about the pivot until reaching a stop, and the clutch mechanism has a second orientation wherein upon continued movement of the trigger, the clutch mechanism permits the drive shaft to rotate the output shaft and cause application of the rotary tack from the magazine.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
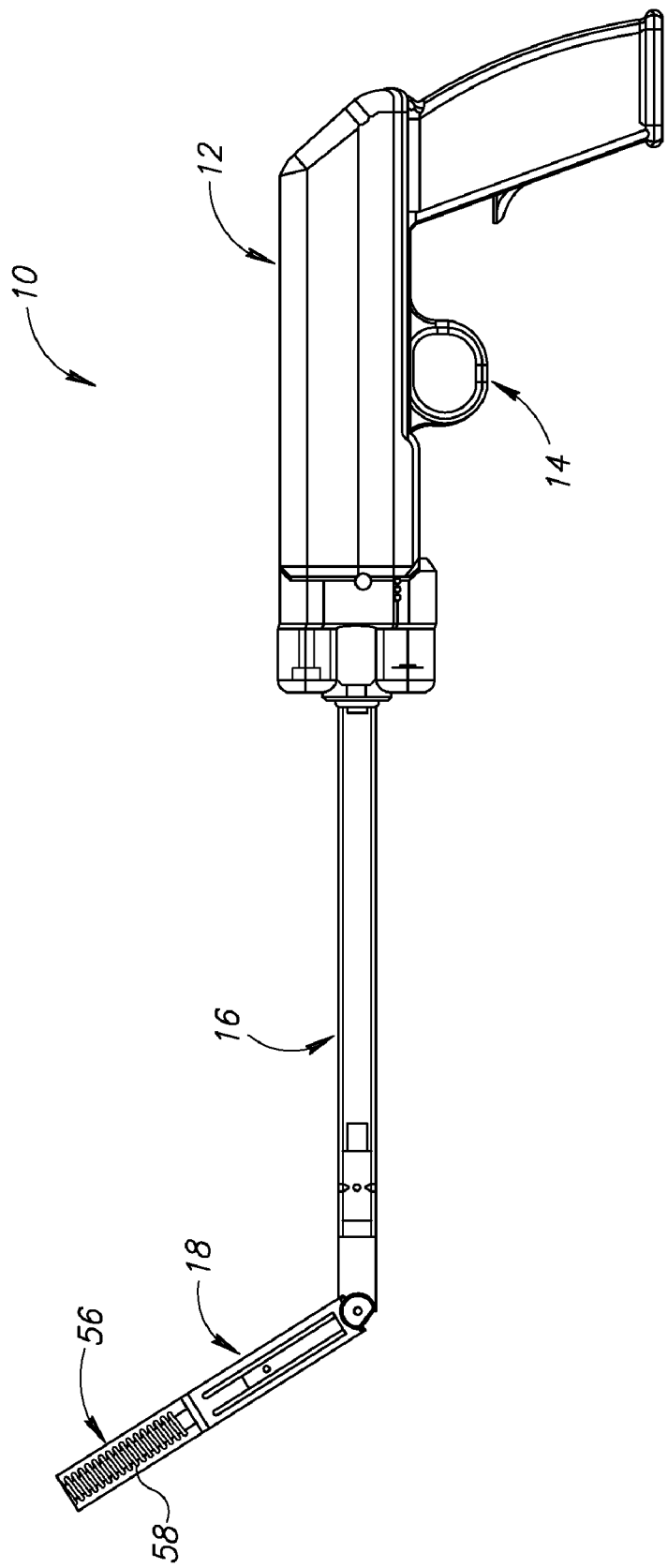
FIG. 1 is a simplified pictorial illustration of a tacker, constructed and operative in accordance with an embodiment of the present invention.

Reference is now made to FIG. 1, which illustrates a tacker 10, constructed and operative in accordance with an embodiment of the present invention.

Tacker 10 may include a handle 12 with a trigger assembly 14, described further in detail hereinbelow with reference to FIG. 8. A drive shaft 16 is coupled to trigger assembly 14. An articulated applicator arm 18, described more in detail hereinbelow with reference to FIGS. 5-7, is pivotally connected to drive shaft 16.

Figure 2:
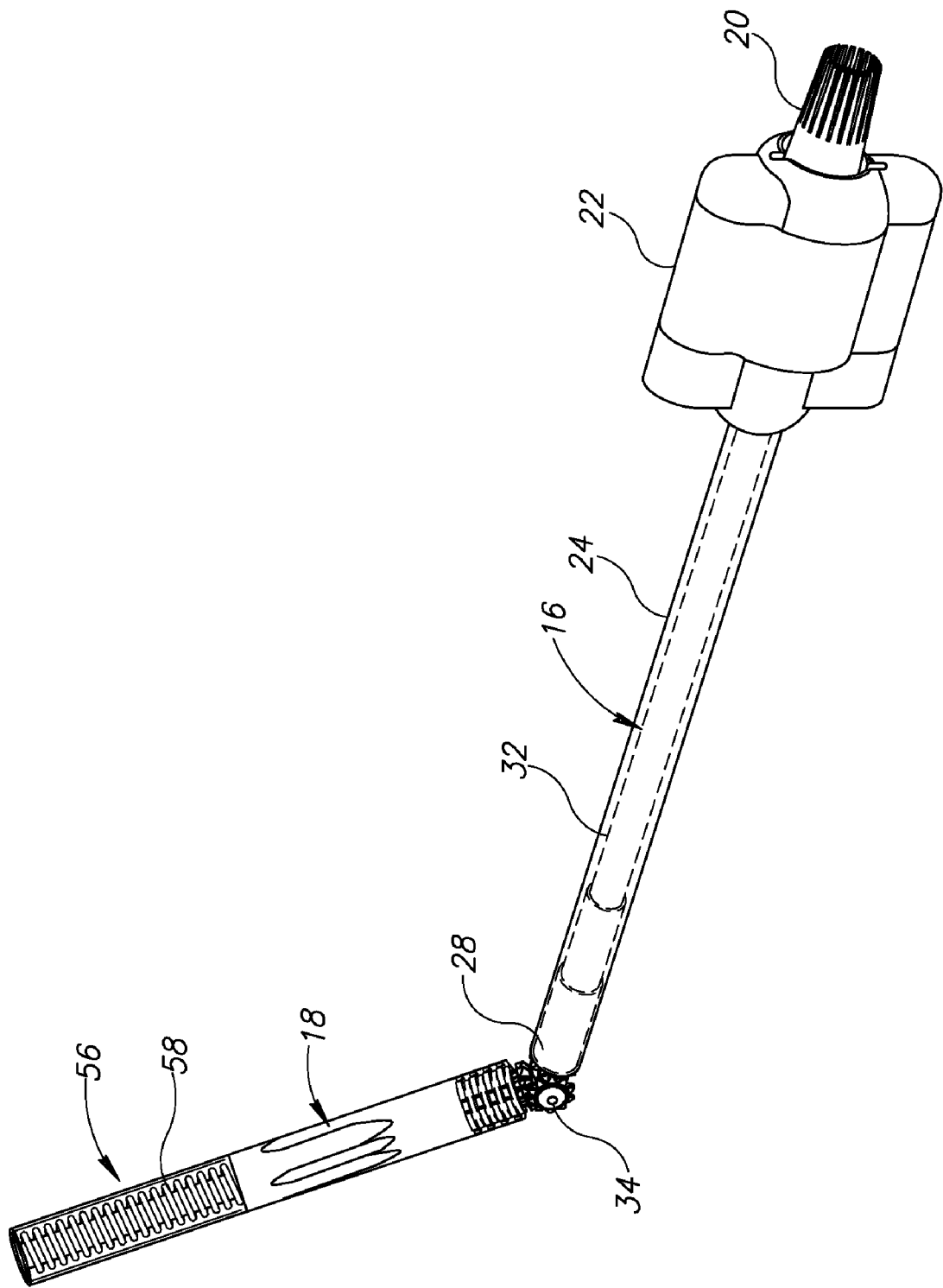
FIG. 2 is a simplified pictorial illustration of a drive shaft with an articulated applicator arm of the tacker of FIG. 1, in accordance with an embodiment of the present invention.
Figure 3:
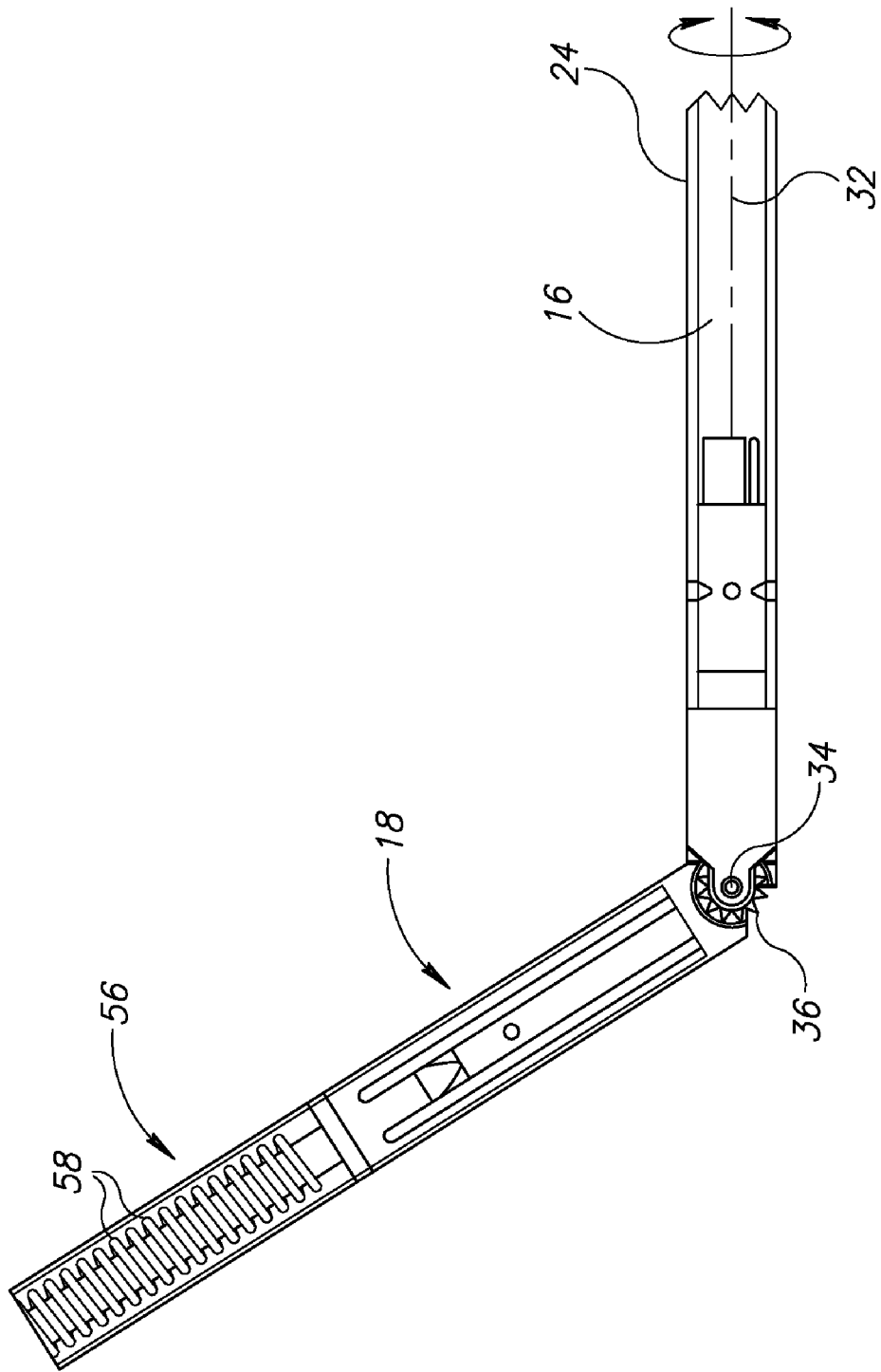
FIG. 3 is a more detailed illustration of the drive shaft and articulated applicator arm of the tacker of FIG. 1.
Figure 6:
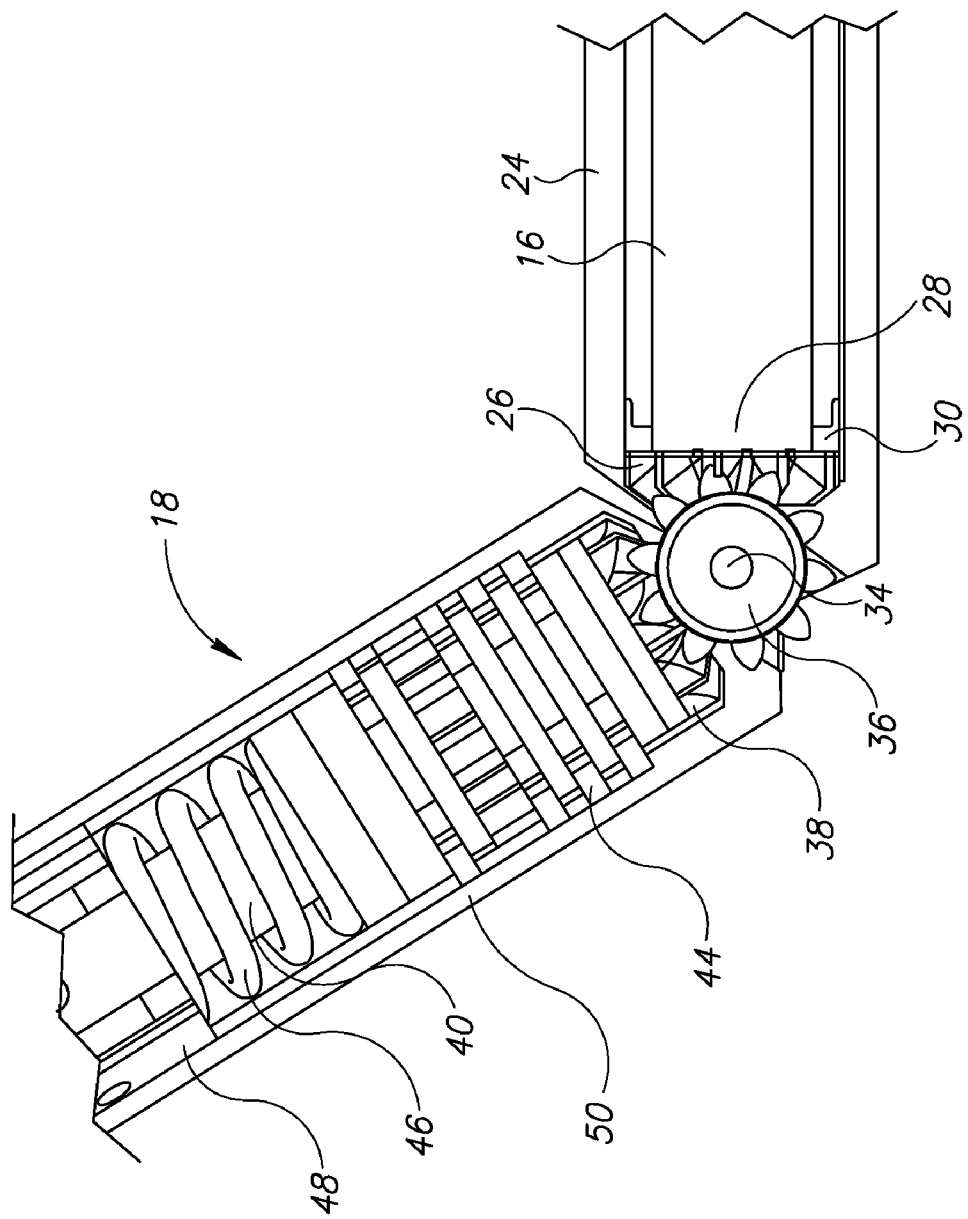
FIGS. 6 and 7 are more detailed illustrations of gear connections for the articulated applicator arm of the tacker of FIG. 1, in accordance with an embodiment of the present invention.
Figure 7:
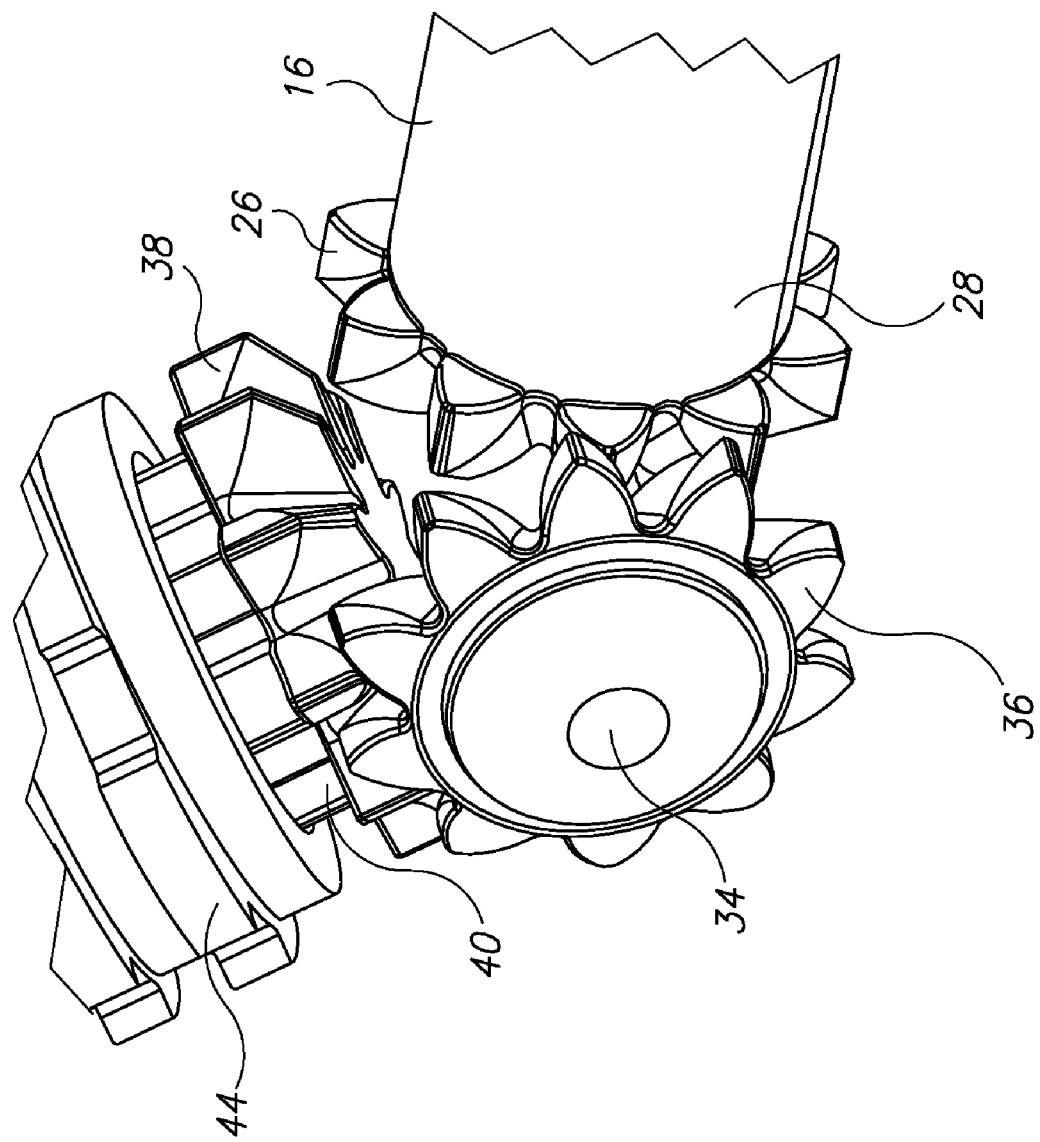

Reference is now made to FIGS. 2, 3, 6 and 7. A proximal end 20 of drive shaft 16 is splined (or otherwise suitably shaped) for mating with trigger assembly 14 (the mating connection being described further hereinbelow with reference to FIG. 8). The proximal end 20 of drive shaft 16 is journaled in a roller bearing housing 22 (FIG. 2). Drive shaft 16 extends through an extension tube (also called housing) 24 and a drive gear 26 is attached to a distal end 28 of drive shaft 16 (FIGS. 6 and 7). The distal end 28 of drive shaft 16 is journaled in a bearing 30 (FIG. 6). Thus drive shaft 16 is arranged for rotation about a longitudinal axis 32 thereof (FIGS. 2 and 3).

Articulated applicator arm 18 is pivoted with respect to drive shaft 16 at a pivot 34 (FIGS. 2, 3, 6 and 7). A spur gear 36 is rotatingly mounted at pivot 34 and meshes with drive gear 26 of drive shaft 16 and with a bevel gear 38 (FIGS. 6 and 7) attached to a rotatable output shaft 40 (also seen in FIG. 5) of articulated applicator arm 18. Accordingly, as drive shaft 16 rotates about its longitudinal axis 32, drive gear 26 turns and causes rotation of spur gear 36. As will be described further hereinbelow, depending on a clutch mechanism, rotation of spur gear 36 either pivots articulated applicator arm 18 about pivot 34 (if the clutch mechanism clutches output shaft 40 and does not permit rotation of output shaft 40) or causes rotation of bevel gear 38 so as to cause rotation of output shaft 40 (if the clutch mechanism is free and permits rotation of output shaft 40).

Figure 4:
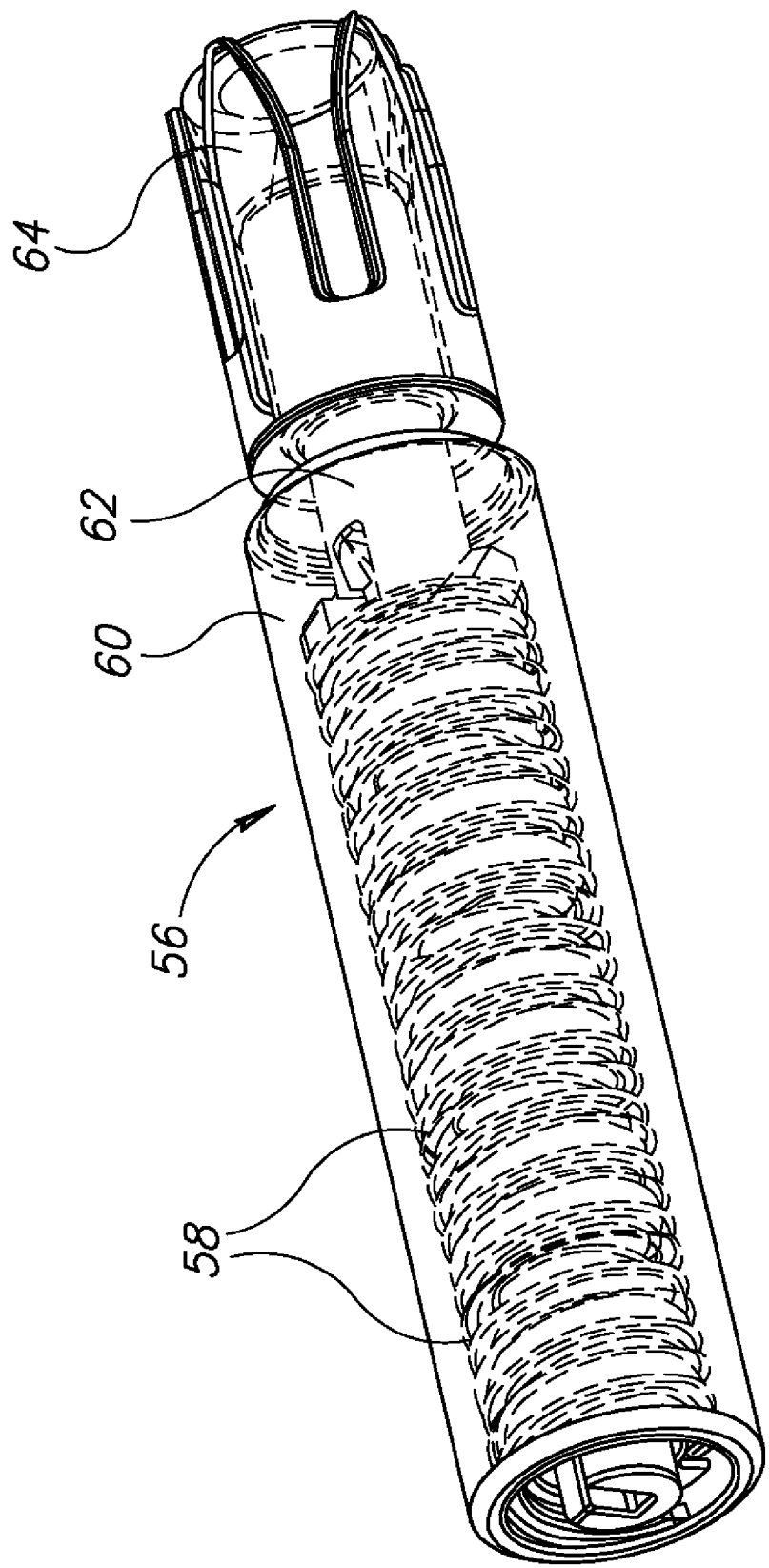
FIG. 4 is a simplified pictorial illustration of a magazine that holds rotary tacks and which attaches to the articulated applicator arm of the tacker of FIG. 1, in accordance with an embodiment of the present invention.
Figure 5:
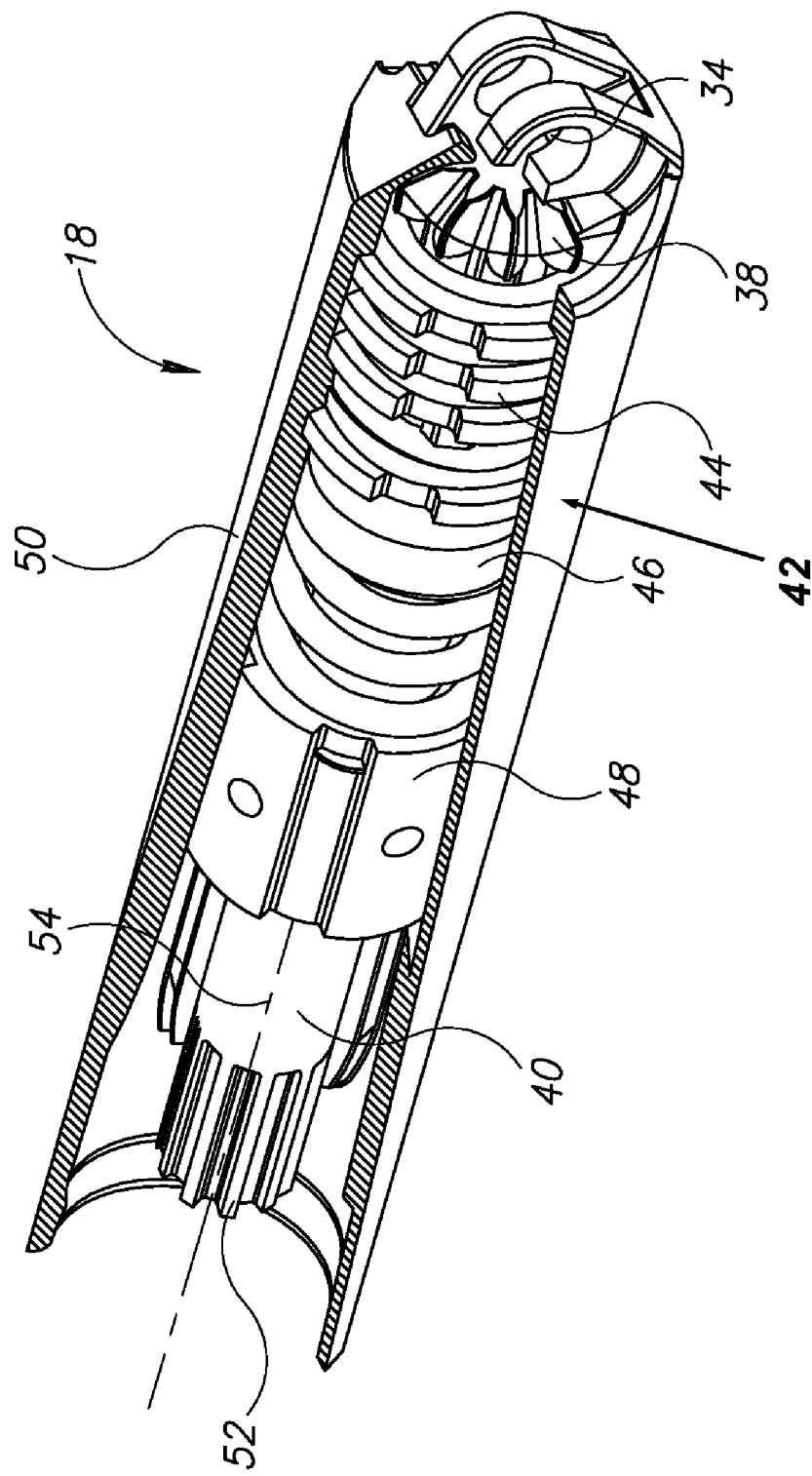
FIG. 5 is a more detailed illustration of the articulated applicator arm of the tacker of FIG. 1, in accordance with an embodiment of the present invention.

Reference is now made to FIGS. 5 and 6. Articulated applicator arm 18 includes a clutch mechanism 42. The clutch mechanism 42 may include a multi-disc clutch 44 with a spring 46 (or equivalent biasing device) mounted on output shaft 40. Spring 46 is biased against an abutment 48. Output shaft 40 is journaled in a housing 50. A distal end 52 of output shaft 40 is splined (or otherwise suitably shaped) for mating with a magazine that holds rotary tacks, described below with reference to FIG. 4. The pivot 34 is at the proximal end of housing 50.

The clutch mechanism 42 is designed (i.e., the seizing strength of multi-disc clutch 44 together with spring 46 on output shaft 40) such that upon initial rotation of drive shaft 16, which starts rotating spur gear 36, clutch mechanism 42 clutches (seizes) output shaft 40 and does not permit rotation of output shaft 40. Bevel gear 38 cannot turn because of clutch mechanism 42, but because the teeth of spur gear 36 are meshed with bevel gear 38, the rotation of spur gear 36 by drive shaft 16 causes the articulated applicator arm 18 to pivot about pivot 34 until the proximal end of housing 50 abuts and stops against the distal end of extension tube 24. FIG. 6 shows the relative position of the parts just before housing 50 abuts and stops against the distal end of extension tube 24. Continued rotation of drive shaft 16 further rotates spur gear 36. Since articulated applicator arm 18 cannot pivot anymore, the rotation of spur gear 36 imparts a turning force on output shaft 40 (via bevel gear 38) that overcomes clutch mechanism 42 and output shaft 40 now rotates about its own longitudinal axis 54 (FIG. 5).

Reference is now made to FIG. 4, which illustrates a magazine 56 that holds rotary tacks 58. Magazine 56 includes a housing 60 in which a tacker shaft 62 is journaled. A proximal end 64 of tacker shaft 62 is complimentarily shaped for mating with the distal end 52 of output shaft 40. For example, the proximal end 64 of tacker shaft 62 may comprise a snap connector which snaps together with the spline of distal end 52 of output shaft 40. One or more rotary tacks 58 are disposed one after the other along tacker shaft 62 (five rotary tacks are illustrated in the exemplary, non-limiting embodiment). Rotary tacks 58 may be held on screw threads formed on tacker shaft 62. When rotation of spur gear 36 imparts a turning force on output shaft 40, this causes rotation of tacker shaft 62, thereby advancing rotary tacks 58 off tacker shaft 62 and screwing them into tissue (not shown).

Figure 8:
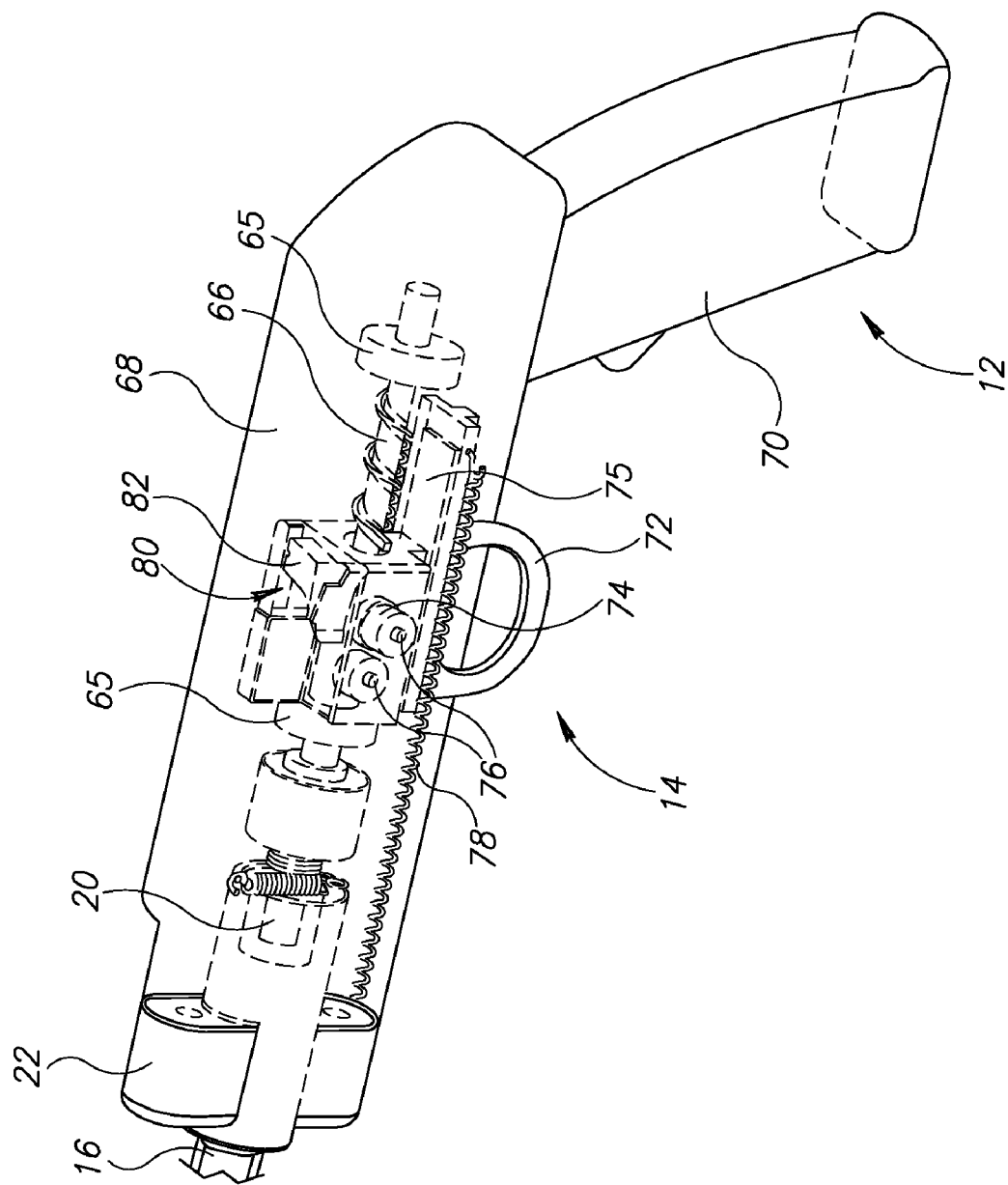
FIGS. 8 and 9 are simplified pictorial illustrations of a handle with a trigger assembly of the tacker of FIG. 1, in accordance with an embodiment of the present invention.
Figure 9:
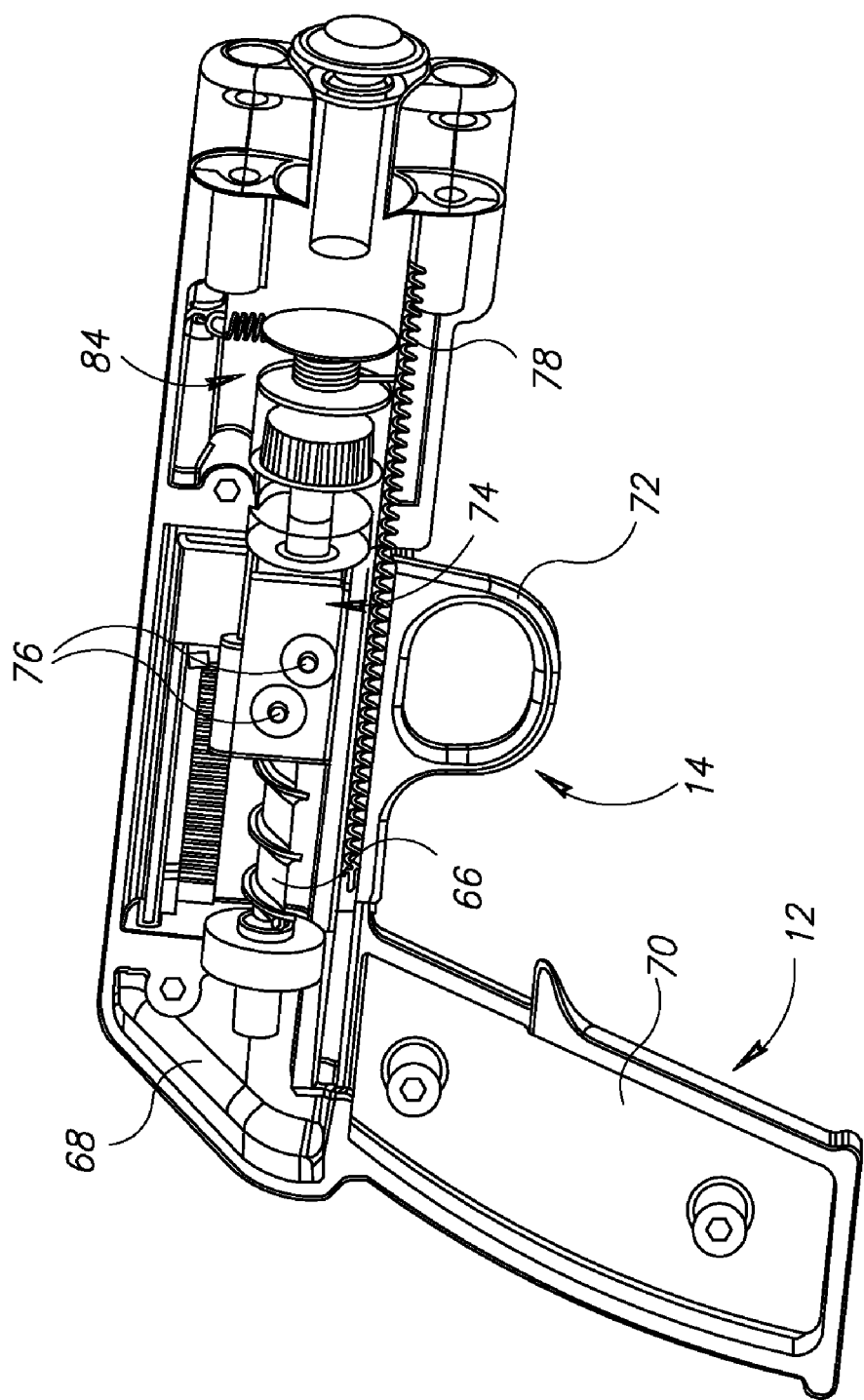

Reference is now made to FIGS. 8-9, which illustrates handle 12 and trigger assembly 14, in accordance with an embodiment of the present invention.

As mentioned above with reference to FIG. 2, the proximal end 20 of drive shaft 16 is splined (or otherwise suitably shaped) for mating with trigger assembly 14. As seen in FIG. 8, the proximal end 20 of drive shaft 16 mates with the distal end of a worm gear drive shaft 66 journaled inside a housing 68 of handle 12 with bearings 65. Housing 68 may be shaped like a hand gun with a pistol grip 70.

Figure 10:
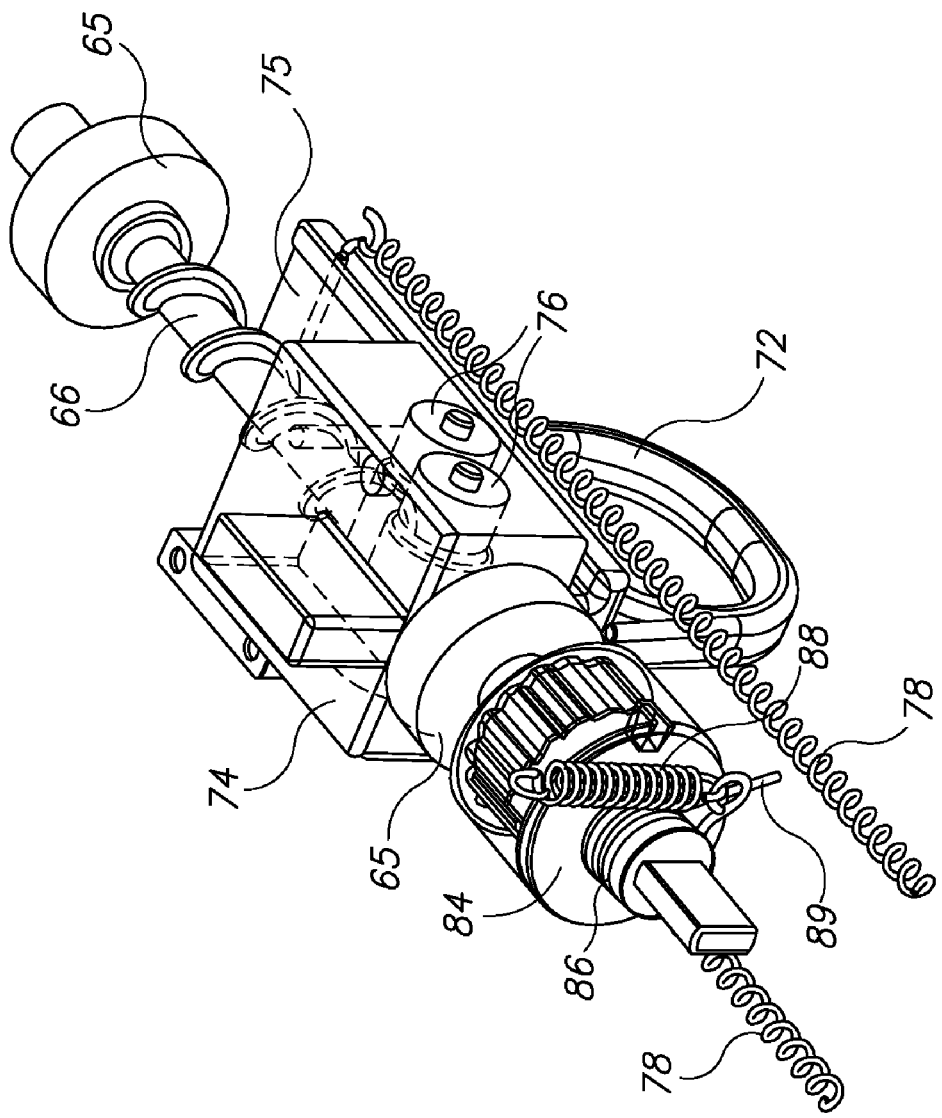
FIG. 10 is a more detailed illustration of a clutch and drive mechanism for the trigger assembly of FIGS. 8 and 9, in accordance with an embodiment of the present invention.

Reference is made additionally to FIG. 10. Trigger assembly 14 includes a trigger 72 connected to a sliding block 74, which may be attached to a plate 75. Block 74 houses one or more gear wheels 76 which mesh with worm gear drive shaft 66. Pulling trigger 72 proximally towards pistol grip 70 moves sliding block 74 backwards (i.e., proximally). When block 74 slides proximally, gear wheels 76 turn in their shafts and cause worm gear drive shaft 66 to rotate about its longitudinal axis, thus imparting rotation to drive shaft 16. One or more return springs 78 may be attached to plate 75 for urging trigger 72 distally back to its initial position after squeezing the trigger to "fire" a tack.

Trigger assembly 14 may include several features for safe, easy one-handed operation. For example, trigger assembly 14 may be constructed such that once the user has started to squeeze trigger 72 and the articulated applicator arm 18 has been pivoted, the trigger 72 will not return inadvertently to its starting position, thus preventing arm 18 from moving accidentally to the wrong place in a surgical procedure. This may be accomplished by providing block 74 with a ratchet mechanism 80, having a pivoted ratchet toggle switch 82. The pivoted ratchet toggle switch 82 has two positions—one that allows the block 74 to slide only proximally (towards pistol grip 70), and the other that allows the block 74 to slide only distally (away from pistol grip 70). Initially pivoted ratchet toggle switch 82 is set in the position that allows the block 74 to slide only proximally. If trigger 72 is not pulled completely back to its proximal limit of travel, the ratchet toggle switch 82 will not permit trigger 72 or block 74 to return distally. When trigger 72 has been fully squeezed and block 74 has reached the proximal limit of its travel, pivoted ratchet toggle switch 82 contacts a pin or an abutment or other suitable immobile structure and pivots to the other toggle position, thereby permitting trigger 72 and block 74 to slide back distally.

Tacker 10 is generally introduced through a trocar or similar instrument. This means articulated applicator arm 18 must be straight with respect to drive shaft 16 for removing or inserting tacker 10 in the trocar. In order to ensure that tacker 10 can always be removed from the trocar even in the event of an emergency or malfunction, trigger assembly 14 may be provided with a safety mechanism that will straighten articulated applicator arm 18 with respect to drive shaft 16 even if trigger 72 is released before reaching its proximal limit of travel. This may be accomplished by means of a clutch mechanism 84, such as a coil spring 86 wrapped around a distal portion of worm gear drive shaft 66 and biased transverse to shaft 66 by another spring 88. When trigger 72 is squeezed, coil spring 86 turns and applies a tensile force on spring 88. Coil spring 86 does not prevent rotation of worm gear drive shaft 66. A tail 89 of coil spring 86 abuts against an abutment or other suitable immobile structure to prevent further rotation of coil spring 86. If trigger 72 is released before reaching its proximal limit of travel, coil spring 86 no longer applies a tensile force on spring 88, and at that moment spring 88 contracts and applies an opposite rotational force on coil spring 86, thereby rotating shaft 66 back. This causes drive shaft 16 to reverse its rotation and thus straighten articulated applicator arm 18 via spur gear 36 at pivot 34 (FIGS. 3 and 6).

Figure 11:
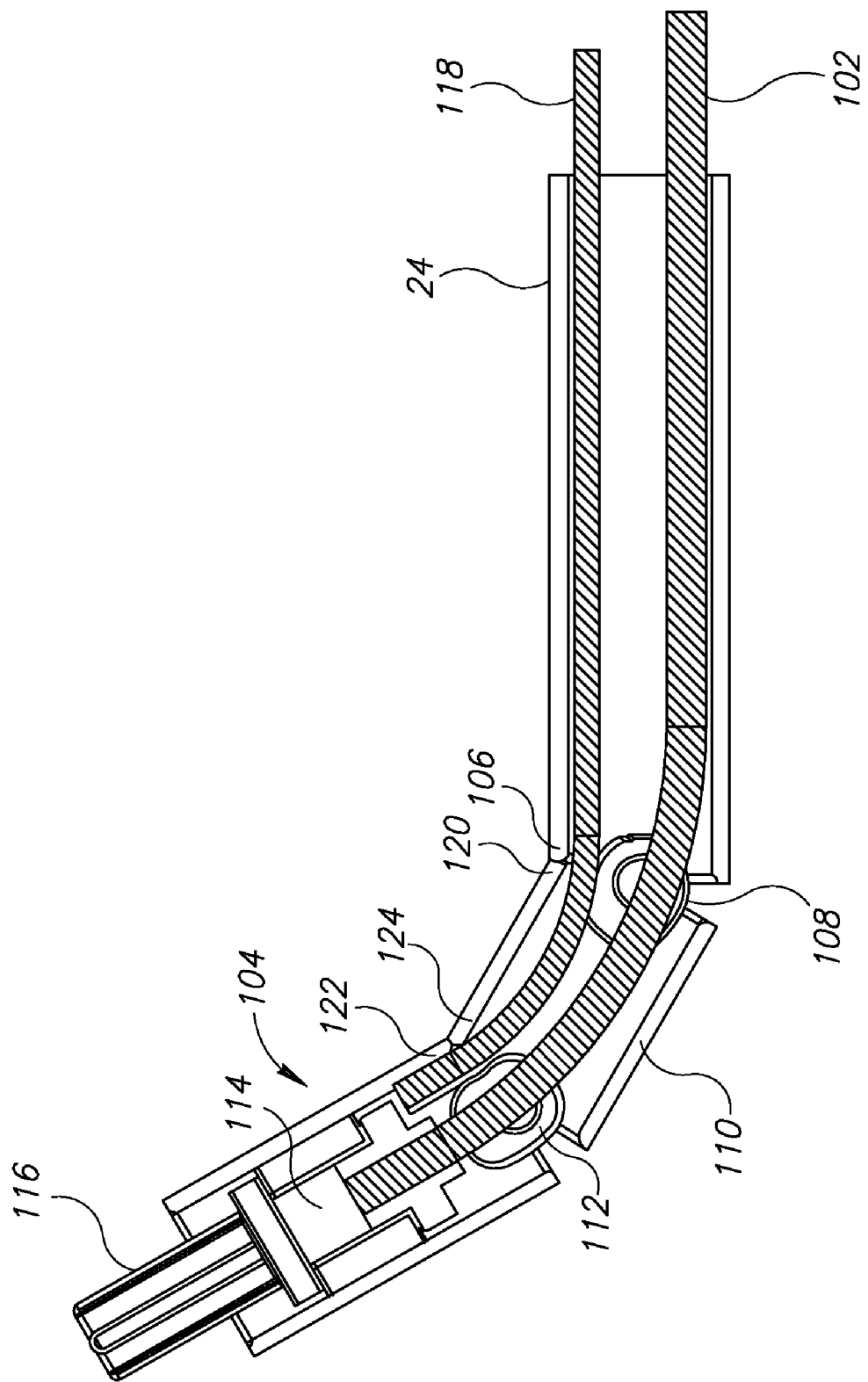
FIGS. 11 and 12 are pictorial illustrations of a drive shaft and articulated applicator arm that uses cable connections instead of gearing, constructed and operative in accordance with another embodiment of the present invention, which may be used with the tacker of FIG. 1, in respective pivoted and straight orientations.
Figure 12:
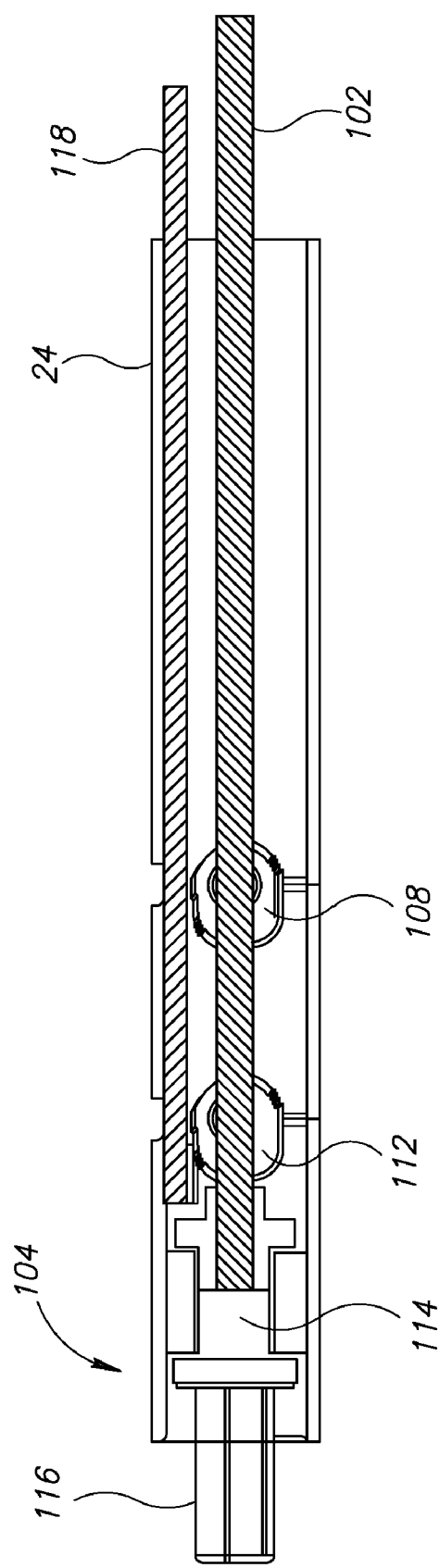

Reference is now made to FIGS. 11 and 12, which illustrate another embodiment of the invention wherein a drive shaft 102 is coupled to an articulated applicator arm 104 with cable connections instead of gearing, as in the previous embodiment.

In this embodiment, drive shaft 102 extends through extension tube or housing 24 and comprises a flexible, rotatable shaft. Drive shaft 102 can be rotated about its longitudinal axis to apply torque and can also be bent. The distal end 106 of housing 24 is pivotally attached by means of a link pivot 108 to an intermediate link 110, which is in turn pivotally attached by means of a link pivot 112 to articulated applicator arm 104. Drive shaft 102 is attached to an output shaft 114 journaled in articulated applicator arm 104. A distal end 116 of output shaft 114 is splined (or otherwise suitably shaped) for mating with the magazine that holds rotary tacks, as described above with reference to FIG. 4.

A pull cable 118 is disposed through housing 24, passes through intermediate link 110 and is attached to articulated applicator arm 104. Both pull cable 118 and drive shaft 102 are attached to a trigger assembly 130, described below with reference to FIGS. 14-15.

This embodiment can be used at a variety of angles, even a straight orientation as shown in FIG. 12.

Figure 13:
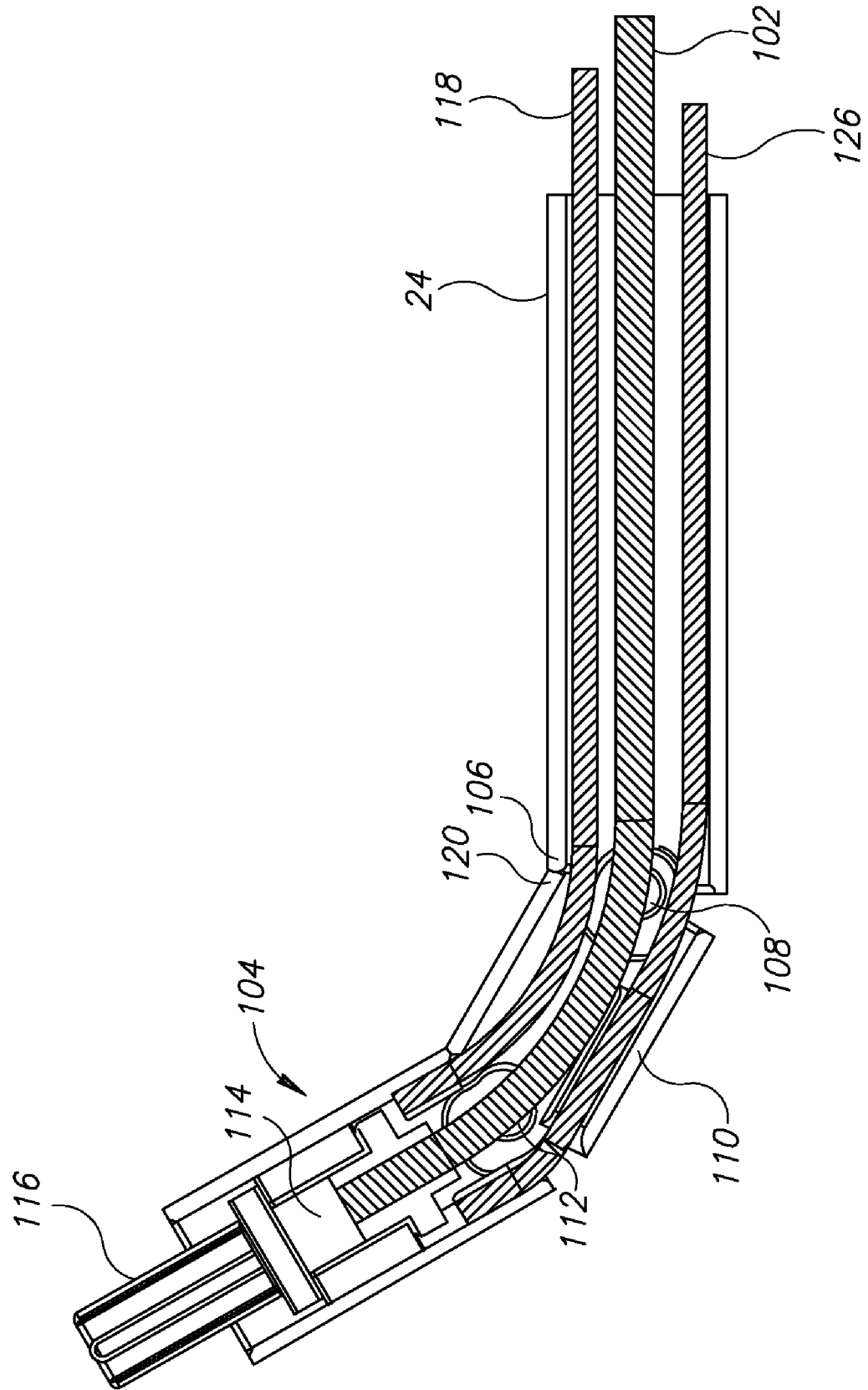
FIG. 13 is a pictorial illustration of a drive shaft and articulated applicator arm, constructed and operative in accordance with yet another embodiment of the present invention, which may be used with the tacker of FIG. 1, in a pivoted orientation, this embodiment using a two cable system.

FIG. 13 illustrates a variation of the embodiment of FIGS. 11 and 12, in which an extra pull cable 126 is provided. Pull cable 126 is also coupled to trigger assembly 14 (not shown) and may be used to give the device added manipulation capabilities.

Figure 14:
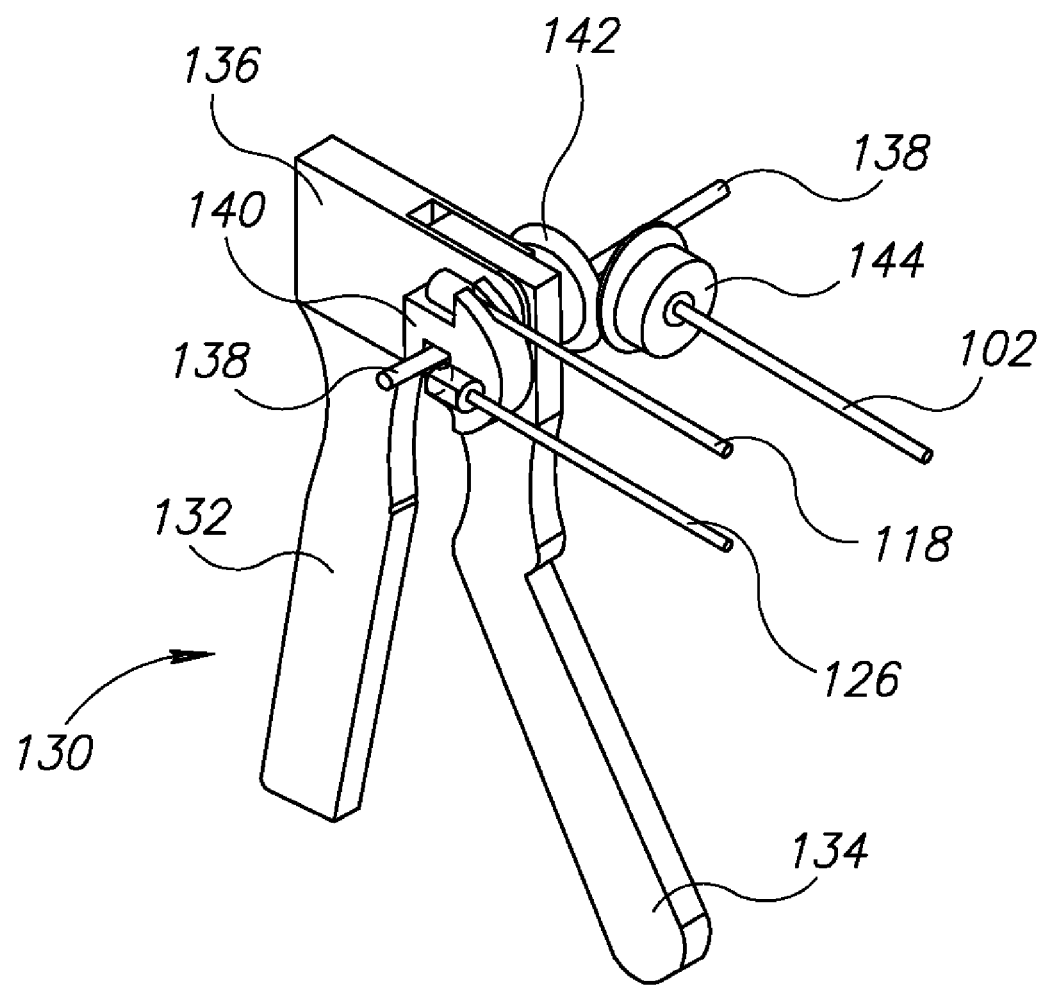
FIGS. 14 and 15 are simplified pictorial and sectional illustrations, respectively, of a trigger assembly used with the drive shaft and pull cable of the embodiments of FIGS. 11-13, constructed and operative in accordance with an embodiment of the present invention.
Figure 15:
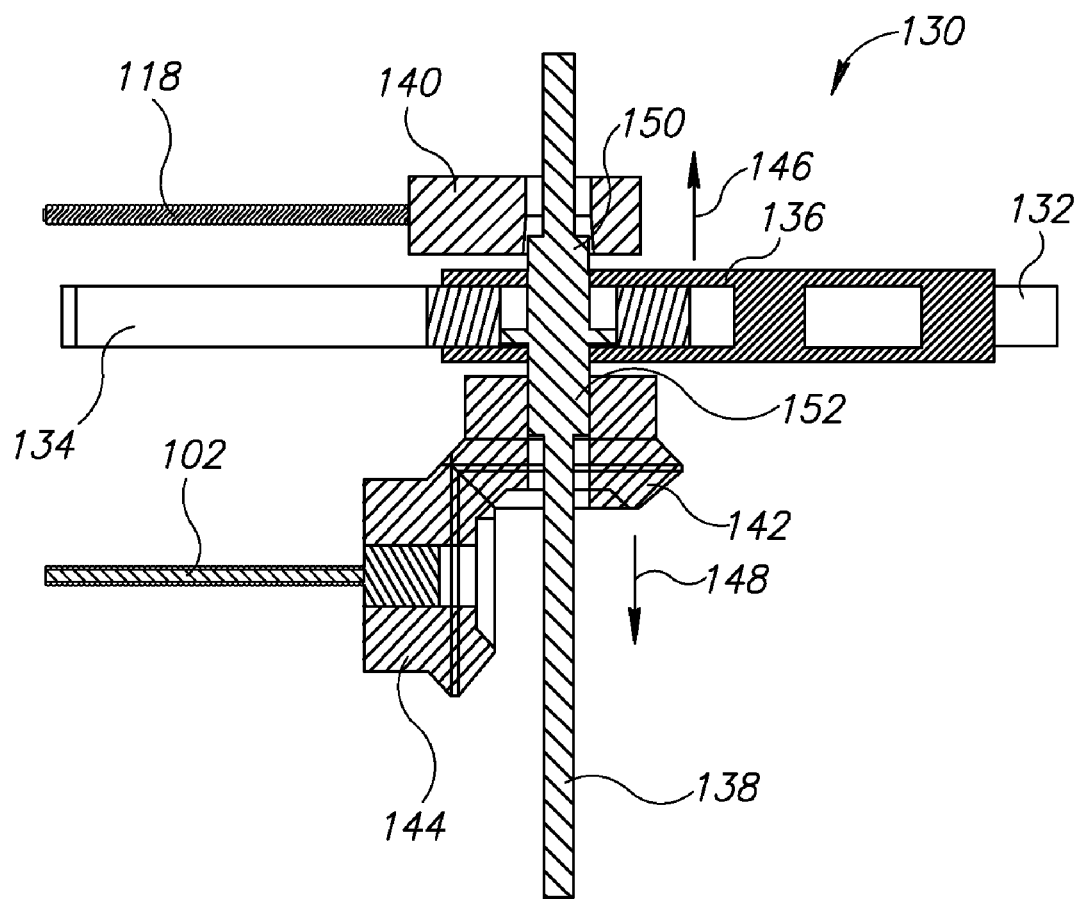

Reference is now made to FIGS. 14 and 15, which illustrate trigger assembly 130, used with the drive shaft 102 and pull cable 118 of the embodiments of FIGS. 11-13, constructed and operative in accordance with an embodiment of the present invention. FIG. 14 shows two pull cables 118 and 126 as in FIG. 13, but one pull cable 118 can also be used.

Trigger assembly 130 includes a static handle 132 and a trigger handle 134 (also referred to as trigger 134). Static handle 132 extends from an upper body 136 in which a catch rod 138 is rotatably mounted. Trigger handle 134 is connected to catch rod 138, such that when trigger handle 134 is squeezed towards static handle 132, catch rod 138 rotates. Catch rod 138 is selectively connectable to either an angulation wheel 140 or a torque gear 142 mounted on opposite sides of upper body 136. Torque gear 142 meshes with another gear 144 to which drive shaft 102 is connected. Pull cables 118 and 126 are connected to angulation wheel 140.

As seen best in FIG. 15, catch rod 138 not only rotates in upper body 136 but also slides from side to side as indicated by arrows 146 and 148. Catch rod 138 has first and second cam extensions 150 and 152, respectively. When catch rod 138 is moved towards angulation wheel 140 (in the direction of arrow 146), first cam extension 150 mates with angulation wheel 140 and second cam extension 152 does not mate with torque gear 142. This is the initial position for operating trigger assembly 130. In this position, squeezing the trigger handle 134 causes angulation wheel 140 to turn, thereby manipulating pull cable 118 or 126. Thus initial pulling of trigger handle 134 pulls pull cable 118 (or 126), which causes intermediate link 110 to pivot about link pivot 108 and articulated applicator arm 104 to pivot about link pivot 112 (FIG. 11 or 13). Catch rod 138 is then moved away from angulation wheel 140 (in the direction of arrow 148), so that first cam extension 150 does not mate with angulation wheel 140 and second cam extension 152 mates with torque gear 142. In this position, continued pulling of trigger handle 134 rotates drive shaft 102 and applies a tack 58 form magazine 56 (not shown here) as described above. Accordingly, in the embodiment of FIGS. 11-15, one single pull of trigger handle 134 pivots articulated applicator arm 104 and actuates the drive shaft 102 to apply the tack. Pivoting is limited by a proximal face 120 of intermediate link 110 abutting against distal end 106 of housing 24 and a proximal face 122 of articulated applicator arm 104 abutting against a distal face 124 of intermediate link 110.

Catch rod 138 is thus a clutch mechanism which, at initial movement of the trigger 134, has a first orientation that causes the articulated applicator arm 104 to pivot about pivot 112 until reaching a stop, and has a second orientation wherein upon continued movement of trigger 134 the clutch mechanism permits the drive shaft 102 to rotate the output shaft 114 and cause application of the rotary tack from the magazine.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A tacker for applying a rotary tack, comprising:
    a drive shaft coupled to a trigger, wherein operating said trigger causes rotation of said drive shaft;
    an articulated applicator arm pivotally connected to said drive shaft at a pivot, said articulated applicator arm comprising a rotatable output shaft connected to a magazine that holds a rotary tack; and
    a clutch mechanism which, at initial movement of said trigger, has a first orientation that causes said articulated applicator arm to pivot about said pivot until reaching a stop, and has a second orientation wherein upon continued movement of said trigger, said clutch mechanism permits said output shaft to rotate and cause application of said rotary tack from said magazine.

2. The tacker according to claim 1, wherein a single full squeeze of said trigger causes said articulated applicator arm to pivot about said pivot and to rotate said output shaft and cause application of said rotary tack from said magazine.

3. The tacker according to claim 2, wherein said trigger comprises a safety mechanism that straightens said articulated applicator arm with respect to said drive shaft even if said trigger is released before reaching its proximal limit of travel.

4. The tacker according to claim 1, wherein a drive gear is attached to a distal end of said drive shaft, and a spur gear is rotatingly mounted at said pivot and meshes with said drive gear and with a bevel gear attached to said output shaft of said articulated applicator arm, wherein upon initial rotation of said drive shaft, which starts rotating said spur gear, said clutch mechanism clutches said output shaft and does not permit rotation of said output shaft and said bevel gear such that rotation of said spur gear by said drive shaft causes said articulated applicator arm to pivot about said pivot until reaching the stop, and wherein continued rotation of said drive shaft further rotates said spur gear which imparts a turning force on said output shaft via said bevel gear that overcomes said clutch mechanism so that said clutch mechanism does not clutch said output shaft and said output shaft rotates and causes application of said rotary tack from said magazine.

5. The tacker according to claim 1, wherein said clutch mechanism, upon initial rotation of said drive shaft, clutches said output shaft and does not permit rotation of said output shaft such that rotation of said drive shaft causes said articulated applicator arm to pivot about said pivot until a proximal end of a housing of said articulated applicator arm abuts and stops against a distal end of a housing of said drive shaft.

6. The tacker according to claim 1, wherein said magazine comprises a housing in which a tacker shaft is journaled, said tacker shaft mating with a distal end of said output shaft, wherein said rotary tack is disposed along said tacker shaft, and wherein rotation of said output shaft causes rotation of said tacker shaft, thereby advancing said rotary tack off said tacker shaft.

7. The tacker according to claim 1, wherein said drive shaft is coupled to a distal end of a worm gear drive shaft journaled inside handle.

8. The tacker according to claim 7, wherein said trigger is connected to a block, said block comprising one or more gear wheels which mesh with said worm gear drive shaft, wherein pulling said trigger proximally moves said block proximally, such that said one or more gear wheels turn and cause said worm gear drive shaft to rotate about its longitudinal axis, thus imparting rotation to said drive shaft.

9. The tacker according to claim 8, further comprising one or more return springs for urging said trigger distally.

10. The tacker according to claim 8, wherein said block comprises a ratchet mechanism including a pivoted ratchet toggle switch that has two positions, wherein one position allows said block to move only proximally and the other position allows said block to move only distally, and wherein when said trigger has been fully squeezed and said block has reached a proximal limit of its travel, said pivoted ratchet toggle switch pivots to the position that permits said trigger and said block to slide back distally.

11. A method for applying a rotary tack, comprising:
    providing a drive shaft coupled to a trigger, wherein operating said trigger causes rotation of said drive shaft, an articulated applicator arm pivotally connected to said drive shaft at a pivot, said articulated applicator arm comprising a rotatable output shaft connected to a magazine that holds a rotary tack, and a clutch mechanism operatively connected to said trigger; and operating said trigger, wherein at initial movement of said trigger, said clutch mechanism has a first orientation that causes said articulated applicator arm to pivot about said pivot until reaching a stop, and said clutch mechanism has a second orientation wherein upon continued movement of said trigger, said clutch mechanism permits said drive shaft to rotate said output shaft and cause application of said rotary tack from said magazine.

* * * * *